(12) United States Patent
Bogie et al.

(10) Patent No.: US 10,653,573 B2
(45) Date of Patent: May 19, 2020

(54) FITTING SYSTEM AND METHOD FOR MODULAR PRESSURE RELIEF CUSHION

(71) Applicant: CASE WESTERN RESERVE UNIVERSITY, Cleveland, OH (US)

(72) Inventors: Kath Bogie, Shaker Heights, OH (US); Tyler Freeto, Marblehead, MA (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 253 days.

(21) Appl. No.: 15/461,520

(22) Filed: Mar. 17, 2017

(65) Prior Publication Data
US 2017/0266071 A1   Sep. 21, 2017

Related U.S. Application Data

(60) Provisional application No. 62/309,595, filed on Mar. 17, 2016.

(51) Int. Cl.
  *A61G 5/10* (2006.01)
  *A61B 5/103* (2006.01)
  *A61G 7/057* (2006.01)

(52) U.S. Cl.
  CPC .......... *A61G 5/1045* (2016.11); *A61B 5/1036* (2013.01); *A61G 7/05707* (2013.01); *A61G 7/05715* (2013.01)

(58) Field of Classification Search
  CPC ....................................................... A61G 5/10
  USPC .......................................... 5/727, 654, 655.5
  See application file for complete search history.

(56) References Cited

U.S. PATENT DOCUMENTS

| | | | | |
|---|---|---|---|---|
| 5,836,027 A | * | 11/1998 | Leventhal | A47C 27/18 5/706 |
| 2008/0201856 A1 | * | 8/2008 | Howard | A47C 27/001 5/690 |
| 2011/0004998 A1 | * | 1/2011 | Losio | A47C 23/002 5/699 |
| 2012/0233784 A1 | * | 9/2012 | Wood | A47C 27/085 5/727 |

\* cited by examiner

*Primary Examiner* — Fredrick C Conley
(74) *Attorney, Agent, or Firm* — McDonald Hopkins LLC (57) ABSTRACT

A high-performance, low-cost modular cushion using range of novel dynamically responsive materials has been designed and developed for use in seating pressure relief. The use of individual contained spheres creates a localized area of gel to minimize both flattening under pressure, and inflating in areas without contact while the elastic nature of the polymers creates a durable system that recovers rapidly from deformation. Gel balls of varying densities have been developed to optimize performance. Quantification of individual ball mechanical properties has been completed which provides load-deflection curves to inform optimal ball array layout based on user interface pressure distributions. A fitting algorithm is proposed which will employ the patient's seating interface pressure distribution to design a personalized modular cushion layout which will evenly distribute contact pressure across seating support interface and maximize contact pressure area.

4 Claims, 6 Drawing Sheets

FIGURE 5

FITTING SYSTEM AND METHOD FOR MODULAR PRESSURE RELIEF CUSHION

CROSS REFERENCE TO RELATED APPLICATIONS

This application claims priority to U.S. Provisional Patent Application Ser. No. 62/309,595, filed on Mar. 17, 2016 and incorporated by reference in its entirety herein.

FIELD OF INVENTION

The present invention relates to an apparatus and method of making customizable pressure-relief cushions designed to minimize the risk to its user of developing pressure ulcers and/or other injuries related to being sedentary on that cushion for prolonged periods of time.

BACKGROUND

A pressure ulcer (pressure injury) is a localized injury to the skin and/or underlying tissue, usually proximate to a bony prominence, developed as a result of a combination of interface pressure, friction/shear, and environmental factors such as moisture and temperature. These ulcers are most commonly associated with diabetics, spinal cord injuries, coma or bed/wheelchair-bound patients, and people who are unable to feel pain from sustained pressure and/or to relieve the pressure/shear that causes the ulcer. Typically, pressure ulcer injuries are categorized by the following stages of severity:

Stage I: Reddening of intact skin that persists despite applied pressure. Stage I pressure ulcers are often coupled with a temperature and/or stiffness change compared to surrounding skin.

Stage II: Damage to or loss of thickness of the dermis, paired with an open wound (broken epidermis). Stage II pressure ulcers can also include open or intact blistering. Generally these pressure ulcers are relatively shallow.

Stage III: Tissue damage and/or loss is full thickness of the skin, down to and including the subcutaneous tissue. Subcutaneous fat may be visible depending on location, but bone, muscle, or tendon are not visible. Underlying fascia is intact.

Stage IV: Damage is severe enough to expose underlying bone, muscle, or tendon.

Unstageable: Exudate, slough, eschar or other debris obscure or fill the wound bed, preventing proper stage assessment until it is removed.

Sitting on a hard surface or lying in bed produce increased pressures under bony prominences, such as the ischial tuberosities, that exceed intravenous capillary pressure. The combined effect cuts off vascular flow to the high-pressure area, thereby increasing pressure ulcer injury risk. Shearing between the skin and bone can twist and occlude small blood vessels, further promoting ischemia, as well as potentially causing blisters and skin damage at the surface. Moisture resulting from incontinence and sweat can also cause maceration and weakening of skin and tissue, although reduced temperatures may alleviate some of these issues.

Once formed, pressure ulcers are difficult to treat, and the cost of such care—even for a single pressure ulcer—may approach $70,000. As of the date of this application, the total cost of all pressure ulcer treatment and prevention across all patient groups is estimated to easily exceed $1 billion per year in the United States alone.

Currently, long-term wheelchair users have a choice of several different types of pressure-relief wheelchair cushion that are designed to reduce the user's risk of developing a pressure ulcer. Most often, cushions are categorized by the main material used in their construction. The five most common materials are standard and viscoelastic foams, gels, viscous fluids, and air.

These materials may be combined in a variety of ways to produce the cushion. For example, some air-inflated cushions, such as the Roho® line of cushions use inter-connected air cells, allowing the air to flow freely inside the cushion. Another line of air-inflated cushion, from Vicar® use individually sealed chambers, preventing cross-flow. The Jay Medical® Jay® 2 cushion uses gel-filled chamber with a foam substrate to provide support and pressure relief. The chamber is filled with proprietary Jay Flow™ gel, which has been shown to provide good postural stability. However, many of these commercial cushions cost $300-$450 or more.

A wheelchair cushion that matches or exceeds the performance of commercial cushions at a greatly reduced cost could provide a value driven engineering solution for effective pressure ulcer prevention and treatment. Further, a method to design, fabricate, and construct a pressure-relief wheelchair cushion that combines the performance strengths of the existing, proprietary cushions with the economy of non-proprietary, widely available materials would be welcomed.

SUMMARY

In one aspect, a customizable, modular cushion for minimizing risk of pressure ulcer formation is contemplated. The modular cushion comprises a foam substrate having a plurality of voids formed in a uniform pattern across a length and a width of the substrate, wherein each void is substantially identical in size and shape and a plurality of gel balls, wherein one ball is provided to one of the voids and wherein each ball has an adjusted viscosity selected based upon individualized pressure maps associated with an individual user.

A further aspect is a method of manufacturing such customized cushions. A pressure map is created based upon an individual user. Portions of the pressure map are associated with a modular array of regularly spaced gel balls, arranged in a uniform array. Individual loading of each ball is determined based upon its location relative to the pressure map while the average pressure on a group of adjacent balls is also concurrently determined. Finally, the viscosity of each ball is adjusted based upon the aforementioned determinations prior to inserting that ball into the array to create the final, customized cushion.

Another aspect contemplates a system of creating customized cushions that reduce risk of formation of pressure ulcers in a user, including a testing apparatus to create pressure maps specific to anticipated, individual users. The customization system also includes a two-part, polymerizable, adjustably viscous fluid, a plurality of gel balls, wherein each ball is adjusted a customized viscosity based upon the pressure map and provided to a specific void in the substrate, and a foam substrate having a plurality of voids formed in a uniform pattern across a length and a width of the substrate, wherein each void is substantially identical in size and shape.

Specific reference is made to the appended claims, drawings, and description below, all of which disclose elements of the invention. While specific embodiments are identified, it will be understood that elements from one described aspect may be combined with those from a separately identified aspect. In the same manner, a person of ordinary skill will have the requisite understanding of common processes, components, and methods, and this description is intended to encompass and disclose such common aspects even if they are not expressly identified herein.

DESCRIPTION OF THE DRAWINGS

Operation of the invention may be better understood by reference to the detailed description taken in connection with the following illustrations. These appended drawings form part of this specification, and any written information in the drawings should be treated as part of this disclosure. In the same manner, the relative positioning and relationship of the components as shown in these drawings, as well as their function, shape, dimensions, and appearance, may all further inform certain aspects of the invention as if fully rewritten herein.

In the drawings.

DETAILED DESCRIPTION

Reference will now be made in detail to exemplary embodiments of the present invention, examples of which are illustrated in the accompanying drawings. It is to be understood that other embodiments may be utilized and structural and functional changes may be made without departing from the respective scope of the invention. As such, the following description is presented by way of illustration only and should not limit in any way the various alternatives and modifications that may be made to the illustrated embodiments and still be within the spirit and scope of the invention.

As used herein, the words "example" and "exemplary" mean an instance, or illustration. The words "example" or "exemplary" do not indicate a key or preferred aspect or embodiment. The word "or" is intended to be inclusive rather an exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggest otherwise.

The materials used in a cushion affect the cushions performance, based on the properties of the material. The five common cushion materials: standard and viscoelastic foams, gel, viscous fluids, and air, all perform differently under loading conditions. Materials such as foams will compress due to load, while fluids, gels and air will flow to areas of low pressure, equalizing pressure in a cell containing a fluid. In addition, properties of these materials may be time and/or temperature dependent, changing the way a cushion behaves based on the how load is applied (loading rates and durations) and the body temperature of a patient.

The construction and design of a cushion also affects its performance. Pressure relief can be achieved using only one material, such as air, or foams of varying densities, or in combination, such as gel-filled cells suspended in foam substrate. Air or fluid-filled cells can be arranged in different patterns or sizes. In one arrangement, the cells are interconnected and arranged in a grid to allow fluid to flow from one cell to the next. Alternatively, cells may be individually sealed so as to prevent fluid flow between cells.

Another major design choice in wheelchair fabrication is whether the cushion is static or dynamic. With static cushion designs, pressure-relief techniques, such as slight repositioning movements performed every 30 minutes to 2 hours, can temporarily relieve pressure and restore flow to body parts at risk of pressure ulcers. However, some studies suggest this type of pressure relief may not be adequate, or may be too difficult for patients to perform themselves, if their limited mobility also affects the upper extremities.

To mimic this function automatically, dynamic cushion designs have been developed. These designs use inflating and deflating air chambers to shift the patient's weight and redistribute pressure, either continuously or over set intervals. Dynamic cushions appear to generate more sustained tissue health benefits over the long term when compared to manual weight shifting, including both interface pressure and increased blood flow. These benefits are likely a result of continuous weight shifting by the cushion, as opposed to manual weight shifting by the patient which occurs only in intervals. However, the dynamic cushions are significantly more expensive than static designs, with some models easily exceeding an order of magnitude in cost.

Cushion fit and customization play a significant role in a cushion's ability to prevent a pressure ulcer, irrespective of design or materials. In air-filled cushions, avoidance of pressure ulcers is highly dependent on proper inflation, a process which must be carried out manually and qualitatively. At the same time, checking the inflation is difficult to do for the user themselves, and can require a second person to be performed accurately.

The present invention relies on a modular cushion design that is custom-fit to the user using low cost materials and techniques. The cushion comprises a plurality of individual cushion balls, with each ball individually selected and placed into a grid of holes formed in a foam substrate. The selection process optimizes pressure distribution over the cushion surface while the user is sitting based upon the individual traits of that user. Ideally, perfectly uniform pressure distribution is achieved, resulting in elimination of areas of high pressure and a significant reduction in the risk of pressure ulcer formation.

In one embodiment, the cushion design consists of a foam block with holes cut to house a hexagonal-close-packed array in the foam block, with each hole receiving a polymeric stress ball. The balls are separately filled with varying compositions of the water-like low viscosity fluid comprising polydimethylsiloxane silicone gel. Each ball is positioned about 40 to 60% within the foam substrate (as measured by the total uncompressed surface area of the ball or by the volume of the ball relative to the volume of the hole within the array), with about 50% preferred in one aspect, so as to ensure positional stability as the balls compress and spread under applied loads due to seating. Notably, the balls are made from a low-cost, mass-produced objects, with minor modifications provided to the balls to achieve the individualized characteristics noted above.

A method for fitting cushions and selecting the individualized balls inherent to certain aspects of the invention is premised on three assumptions:
1) Each ball in the cushion compresses independently from all the other balls.
2) Swapping out balls in the cushion will not significantly affect the compression of a given ball relative to the balls around it.
3) If each ball supports the baseline average load across all balls, the user's weight is uniformly distributed, and the best possible result has been achieved.

Thus, in the method of making the cushion, an interface pressure map is created based on the individual ball load-displacement characteristics. The user sits on a baseline cushion filled with 33 standard type balls and data as to variations in pressure across that baseline cushion are recorded over a period of time, such as 2-5 minutes. Areas of interest on the pressure map thus created are selected and defined to correspond to individual balls or groups of balls in the array. The mean pressure on each ball over extended periods of time is then calculated.

This mean interface pressure data for each ball is compared against the individual ball load-displacement curves, so as to approximate the compression (in mm) experienced by each ball in the baseline cushion. If a ball experiences exactly 0 N and is never under any load, its displacement is set to 0 mm. If a ball experiences small loads, such as 0-2 N, the smallest value of force for which load-displacement data exists load is rounded up to the top end of the range (e.g., 2 N). If a ball saturates at a maximum pressure, such as greater than 17N, that particular ball it is set to the maximum value selected.

Next, the mean load across all the balls in the array (e.g., 33 balls) in the baseline modular cushion. The displacement which would be experienced by each of the 5 types of ball at the mean load is determined. The cushion fitting algorithm then compares the approximated displacement levels of the baseline modular cushion, to the levels of displacement for each type of ball that would produce the target average load. For each ball position, the cushion fitting algorithm selects the ball type which would produce the closest to the mean load. Any ball from the baseline modular cushion that experiences 0N is assigned "Ball Type 0", which means that that position may be left empty without affecting the load distribution of the fitted modular cushion.

Figure 1:
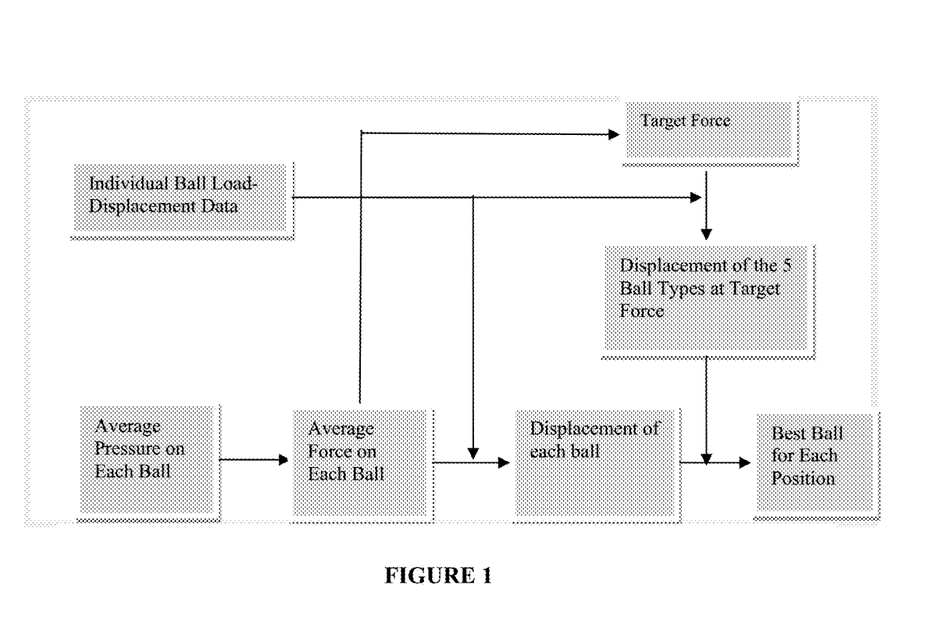
FIG. 1 is a schematic flowchart illustrating how individualized traits for each component of the cushion may be selected.

This process is illustrated in FIG. 1. Individual ball load displacement data and average pressure on each ball are separately observed. The average pressure is then normalized to determine an average force on each ball, with this result informing: 1) the displacement experienced by the ball, and 2) a determination of the target force range for that ball (note: the displacement data is leveraged to identify the range of each ball). Groups of adjacent or related balls (5 are shown in FIG. 1, although any combination of adjacent balls are possible) are considered to calculate the displacement of the group. The individual and group displacement results are compared in order to select the appropriate characteristics for each ball within the overall array.

In this manner, the fitted areas of high pressure become softer due to placement of lower elasticity balls, while areas of low pressure become stiffer due to placement of higher elasticity balls. The net result is an increased contact area which relieves peak pressure, e.g., in the ischial region. The average pressure across all balls also decreases dramatically in comparison to standard, static cushions, thereby demonstrating the versatility of the modular approach to the cushion's design.

Based upon, each modular cushion can be personalized for the user to optimize interface pressure distribution. Notably, an array comprising 36 balls was used, but the methodology can be applied to arrays having smaller or greater number of elements, with arrangements using 25-49 holes or receiving voids for each ball contemplated. In each case, the bifurcated approach of considering each ball, as well as the adjacent groupings, enables an optimized fit that is individualized to each user.

The modular cushion uses a range of novel dynamically responsive materials contained in highly deformable polymeric spheres (gel balls) combined with a supporting substrate. A preferred cushion design includes a maximum unloaded cushion height of 4.25", leading to a maximum gel ball diameter of 2.5" (3" foam base+radius of gel ball). This height represents an optimal combination of overall cushion thickness, customization, and dimensions for equipment where such customized, low cost cushions are expected to deliver the most benefit (e.g., wheel chair seat cushions).

The gel balls to be used have high viscoelastic deformability and low thermal coefficient. Base polymers will consist of soft high performance polyethylene that is both elastic and tacky. Soft base polymers will be utilized to retain comfort, while the tacky surface of the polymers allows individual contained gel sphere to "melt" into one confluent gel filled system when bearing weight and pressed into contact with each other; thus minimizing the development of additional pressure points during use. The elastic nature of the polymers will create a durable system that recovers rapidly from deformation.

The internal viscosity of the gel balls is modified by injection of water soluble monomer units and cross-into the spheres with a syringe. The (poly)dimethyl siloxane is polymerized within the sphere, for ease of fabrication. Varying the monomer to cross-linker ratio enables precise control over both the modulus and density of the gels.

The use of individual contained spheres creates a localized area of gel to minimize flattening under pressure, and does not change in areas without contact. The density of individual balls can be varied to optimize pressure distribution in a specific area In order to reduce the overall cushion weight, some or all of the gel ball inserts may be replaced with additively manufactured silicone/air balls which enables construction of balls with controllable compression properties which are approximately 50% lighter for the same compression response. Inserts have been constructed with varying inner perfactories that modify the stiffness by up to 40%, replicating the variation in the 5 gel ball classes. Such inserts can be made with increased 'tackiness' on one half so that they hold in the wells securely.

As noted above, different viscosities of gel may be employed on a ball-by-ball basis within the substrate, relying on the grouping methodology described herein.

Figure 2A:
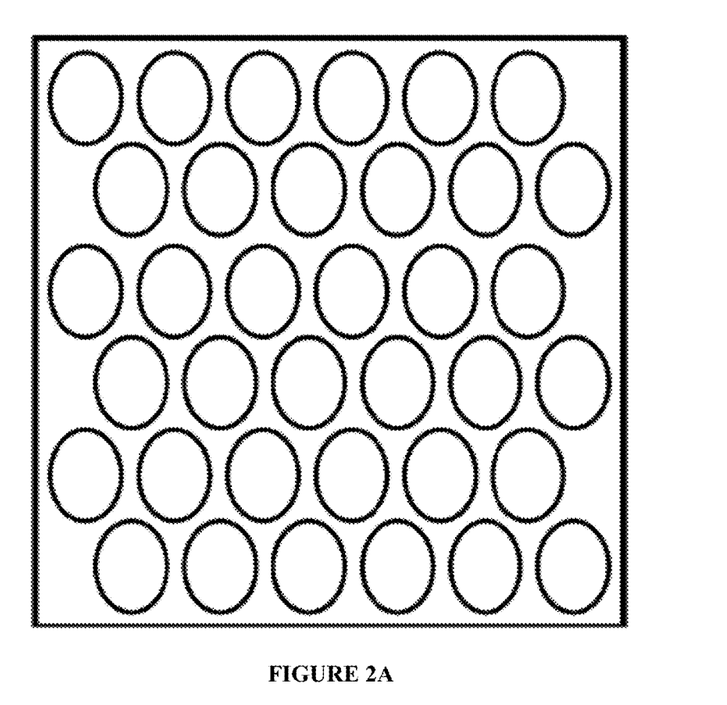
FIGS. 2A and 2B illustrate, respectively speaking top plan and cross sectional side views of the arrangement of receiving voids in a foam substrate according to certain aspects of the invention.
Figure 2B:
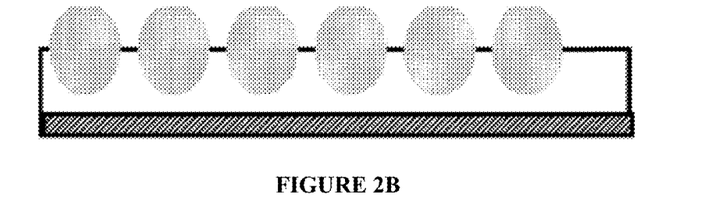
Figure 3A:
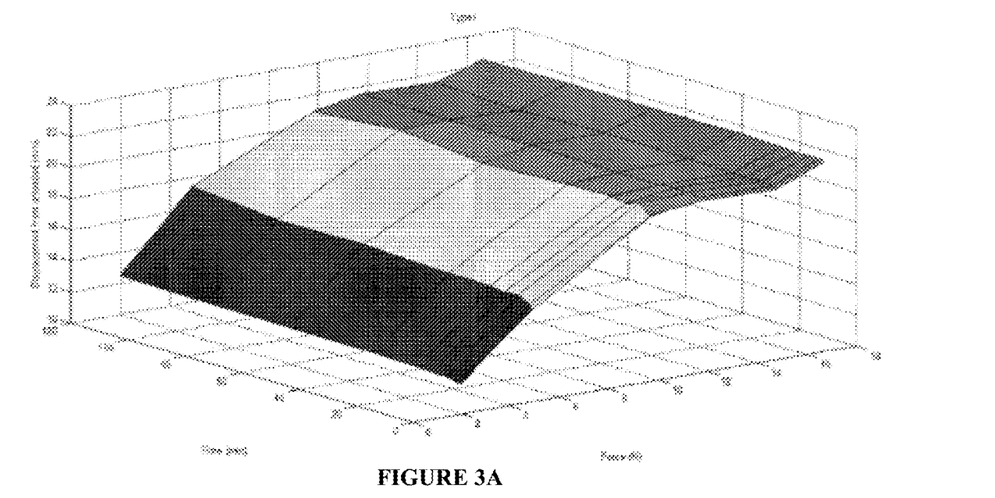
FIGS. 3A through 3E are three dimensional surface plots for compression testing of gel balls of varying compositions.
Figure 3B:
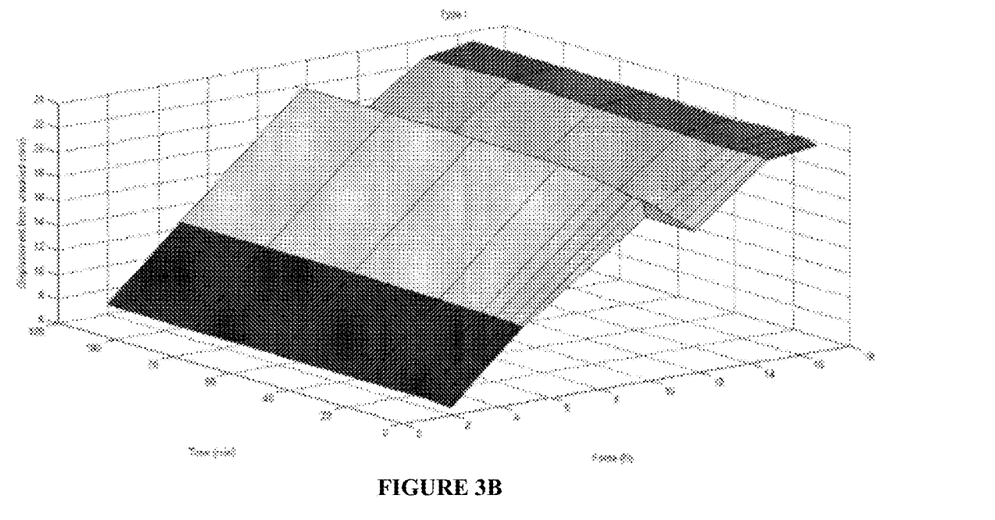
Figure 3C:
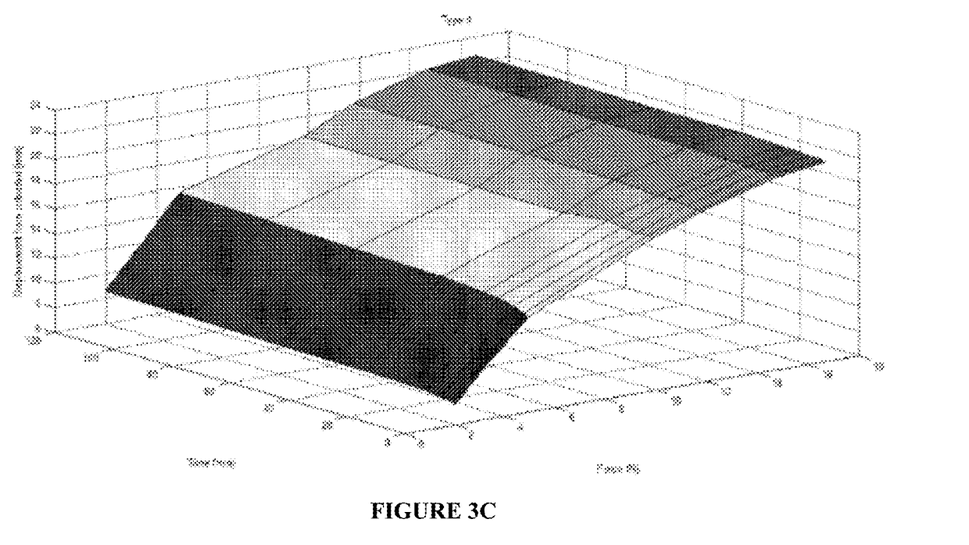
Figure 3D:
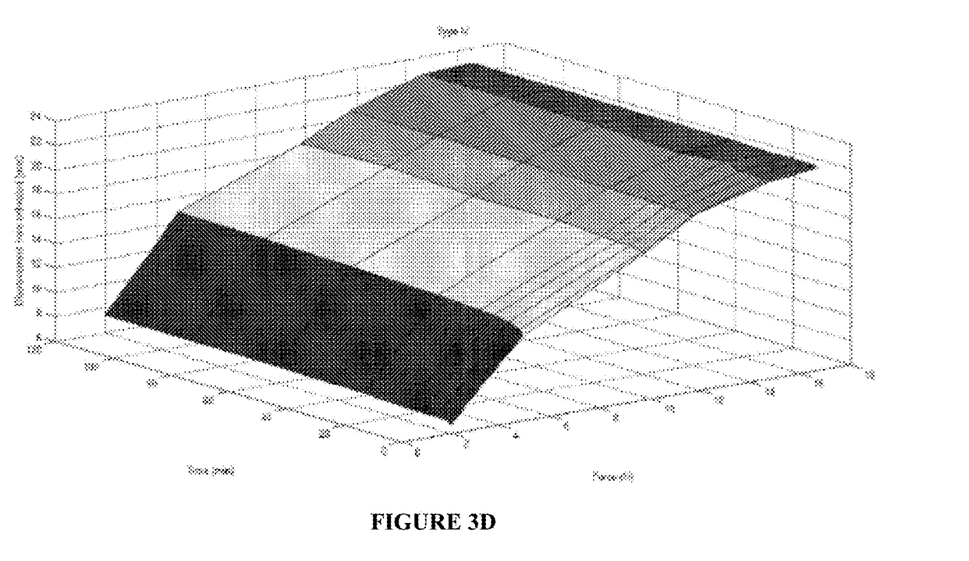
Figure 3E:
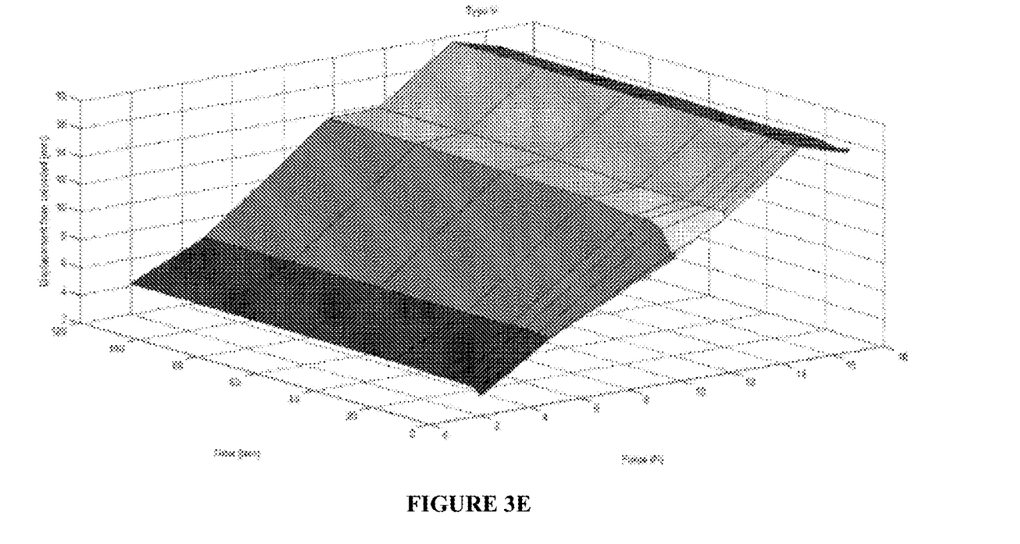
Figure 4A:
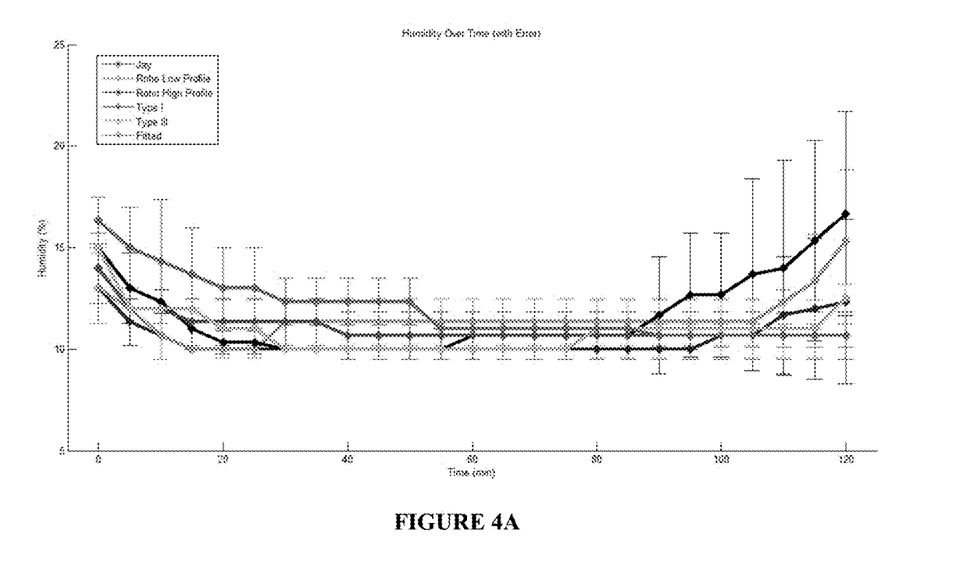
FIGS. 4A through 4C show comparative data for testing of cushions at varying temperatures and humidity.
Figure 4B:
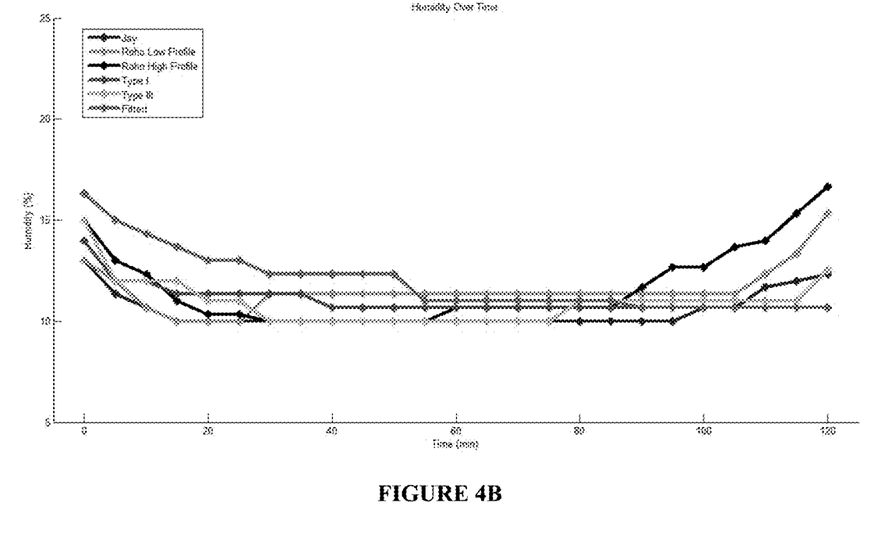
Figure 4C:
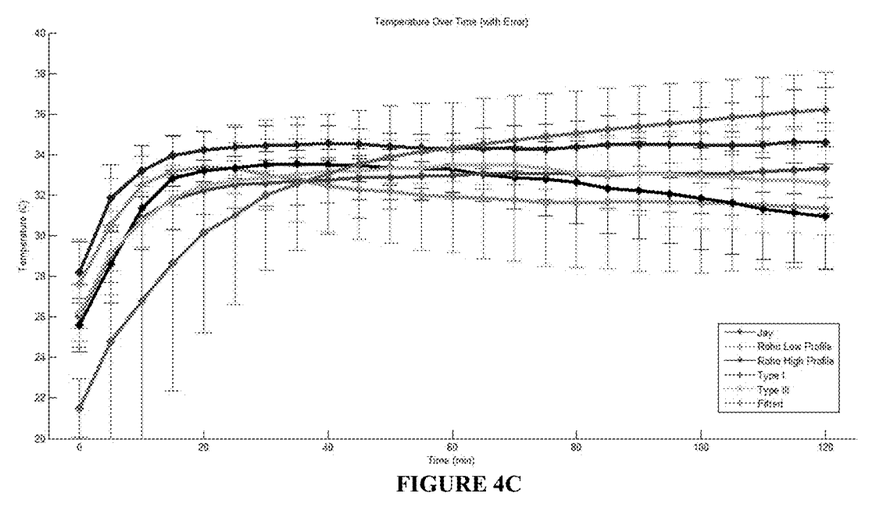

The balls are arranged in a uniformly spaced array, based in part on the assumptions above. In a preferred embodiment, this array is formed in a substrate 20 comprises a square with six alternately offset rows or receiving voids 22 having an arrangement of six holes for securely positioning the balls, as shown in FIG. 2A. As such, uniform distribution with on-center spacing and hexagonal packing is preferred, although other arrangements may be possible, particular for cushions in which square or symmetric (e.g., circular) shapes may not be required. FIG. 2B shows an exemplary cross sectional side view showing balls 24 resting in the substrate 20 with sufficient separation to avoid contact in an uncompressed state, with a base layer 21 of differing thickness and firmness providing additional structure.

Each hole/void 22 is filled with a pliable ball or sphere 24 having a polymeric outer skin containing a fluid or silicone gel. In one aspect, balls can be simple, squeezable "stress balls" that are commonly sold as office toys. These stock balls selected are approximately 2.5" in diameter and hold approximately 100 mL of volume with a flexible polymer skin. The exact composition of the fluid inside the balls is a dyed, watery, low-viscosity fluid, with mechanical properties closely resembling water.

Sylgard® 170 Silicone Elastomer from Dow Corning® was chosen to fill the balls. This silicone comes in a two-part mix, which, when mixed well in a 1:1 ratio will cure and produce a stiff silicone polymer. The curing reaction can occur either over the course of a few hours at room temperature, or as little as 15 minutes when heated to 70° C. The use of this particular silicone is exemplary, and any mixture allowing for the variably controllable creation of viscous fluids is contemplated.

Both parts of the silicone are fluids with relative density 1.33, i.e. denser and more viscous than water. Part A is black with a viscosity of 5,000 mm$^2$/s and contains: dimethyl siloxane, dimethylvinyl-terminated (CAS 68083-19-2), quartz (CAS number) 14808-60-7, and Carbon Black (CAS 1333-86-4). Part B is light grey in color with a lower viscosity at 2,500 mm$^2$/s and contains dimethyl siloxane, dimethylvinyl-terminated (CAS 68083-19-2), quartz (CAS 14808-60-7), dimethyl, and methylhydrogen siloxane (CAS 68037-59-2). When mixed, the two parts undergo a curing polymerization reaction which can produce anything from a fluid gel that is slightly more viscous than Part A alone, to a stiff and solid polymer.

(Poly)dimethyl siloxane ((poly)dimethyl siloxane) oil was also used in ball filling composition testing. The oil is comprised of long chains of (poly)dimethyl siloxane that do not contain any reactive groups, and therefore cannot be polymerized during the curing reaction between Parts A and B of the Sylgard®. The unreacted chains act as spacers, increasing the distance between the cured polymer chains, reducing the cured polymer's stiffness. The oil was used during initial ball filling testing, but was not utilized past this point.

Qualitatively, the addition of relatively high quantities of the (poly)dimethyl siloxane oil decreased the stiffness of the cured polymer slightly. However, the surface of the cured polymer disks with high oil content remained oily, suggesting that as the silicone cured, the oil would float to the surface, and not mix homogenously with the cured polymer.

It was found that the stock ball fluid and Parts A and B of the Sylgard® are immiscible. Thus, all mixtures containing Part A, Part B, and the stock fluid resulted in the Sylgard® curing to form the stiff polymer inside the ball, setting to the bottom due to gravity. The solid polymer was mobile inside the ball, but was still too stiff to make a suitable sitting surface. Mixtures containing only Part A or Part B and the stock fluid resulted in droplets of the thicker silicone monomer suspended in the stock fluid. No curing occurred in these balls, and even relatively high percentages, up to 75%, of Part A or Part B resulted in the ball retaining mechanical properties similar to the stock balls, although these suspensions settled and required additional mixing to re-suspend the droplets.

Foam substrate 20 may be made of open-cell polyurethane foam (PUF) serves as the supporting substrate for the balls. The supporting substrate includes a firm base layer and a containment layer. In one configuration, 1" thick firm PUF (N90) was used for the base layer. 2" thick PUF of medium density (C44) was used for the containment layer.

The best results were obtained when mixing Parts A and B inside the balls in a very unequal ratio, in favor of Part A, without using any stock fluid. Mixtures used of this type consisted of a 1:30 (3.5 mL and 96.5 mL), 1:15 (6 mL and 94 mL), and 1:10 (9 mL and 91 mL) ratios of Part B to Part A. These balls were drained of all 100 mL of stock fluid, and filled with Parts A and B. After injection, the balls were thoroughly mixed via squeezing the balls, and left to cure overnight. The cured silicone produced results ranging from a viscous fluid that is barely thicker than Part A alone, to a compressible solid.

A total of five promising filling mixtures were identified (see Table 1) ranging from the most compliant Type I stock balls to the stiffest Type V. These five mixtures were identified as being qualitatively appropriate for creation of the cushion, while providing a wide range of compliances. Quantitative assessment of the five chosen mixture's mechanical properties was used to characterize the balls.

TABLE 1

| Ball Type | Composition |
| --- | --- |
| I | Stock balls |
| II | 100 mL of Part A of the Sylgard ® |
| III | 1:30, Part B to Part A |
| IV | 1:15, Part B to Part A |
| V | 1:10, Part B to Part A |

To assess the compressive properties of each type of ball filling, a custom piston-like test rig was constructed. The test rig consisted of a short length polyvinyl chloride (polyvinyl chloride) pipe, attached to a wooden base and having a diameter only slightly larger than that of the ball. The wooden base includes circular indentation having a diameter that cooperates with the diameter of the ball to provide a place to rest in the center of the pipe. An insert assembly rests inside the pipe and slides freely along it. This disk, and an attached wooden dowel, serve as a piston.

Each ball was placed in the indentation in the bottom of the pipe, and known compressive force was applied over predetermined periods of points of time (0, 1, 5, 10, 15, 30, 60, 90, and 120 minutes) and mass (0 g, 200 g, 500 g, 1000 g, 1200 g, 1500 g, and 1700 g).

The distance the disk moved during these conditions was recorded and displacement under load was normalized relative to the unloaded displacement. The average and standard deviation of each displacement was determined for each ball type.

Surface plots for each ball type were generate, as shown respectively speaking in FIG. 3A through 3E. Generally speaking, the balls which are qualitatively more solid compress less than the more fluid balls for a given applied load and application time. Balls of Types III and IV behaved very similarly. Type I balls compressed more under a given load and application time compared to the other balls. Type V balls compressed less under a given load and application time compared to the other balls. As the applied load increased, the differences between the ball types decrease.

Also, time was not a major factor in determining the displacement a ball underwent as a result of load, and creep was not a major factor in the ball displacement, especially after the first 5 minutes of loading. This implies that any time-dependent mechanical properties seen in the test cushions is a result of the foam substrate. Time-dependence seen in the complete test cushion is unlikely to be affected by varying the type of ball used in the test cushion.

In order to minimize pressure over the surface of the cushion, all balls in the array should be loaded equally, totally eliminating any high pressure points between the cushion and the user. The cushion laboratory tests outlined in ISO 16480-2 utilize two differently shaped cushion indenters, with known geometries. These indenters are shaped to mimic either the flesh or bony prominences of the patient. Applying a load through these indenters results in some areas of a cushion being compressed more than others, creating areas of high pressure. Placing highly compressible balls under the high displacement areas of an indenter, such as the ischial tuberosity region, will relieve the pressure in these regions. Areas that undergo very little displacement can support more load with a more solid ball to help equalize the pressure over the entire cushion surface, minimizing any high pressure areas.

The modular cushion is designed to be simple to fabricate a predetermined number of thru-holes 22 in cut into the foam substrate 20. The cushion can then be customized and fitted by filling each hole with one of the five different types of ball.

A key aspect of the cushion's design is its ability to be fitted and customized to the patient who is using it. This is achieved by selecting the type of ball to place in each hole in the foam substrate to optimize pressure distribution over the cushion surface while the user is sitting. A perfectly uniform pressure distribution would result in no areas of high pressure, thus decreasing the risk of pressure ulcer formation.

As areas of high pressure become softer due to placement of lower elasticity balls, while areas of low pressure become stiffer due to placement of higher elasticity balls. The net result is an increased contact area which relieves peak pressure such as in the ischial tuberosity region. The average pressure across all balls in the array also decreases.

One benefit of the modular cushion disclosed herein resides in its potential to minimize the overall cushion cost to the consumer. This potential reduction in cost not only includes the initial outlay for customizing and manufacturing a new cushion but also factors in the cost and expected frequency of cushion component replacement and the functional life of the cushion as compared to other currently available products. A preliminary cost analysis indicated, assuming the gel balls would be the cushion component with the shortest lifetime (possibly as short as 4 to 6 months), the overally annual cost for the inventive modular cushion is still nearly 70% less than the commercially available high-performance cushions' estimated yearly cost including replacement components (where such replacement is even feasible/applicable). Therefore, one advantage of the modular cushion concept is that it allows replacement of a single ball at a time, without having to replace the entire cushion. In the event of an early failure of one of more balls, they can readily be replaced to retain function. Normal foam degradation and cover wear will mark the end of the cushion's lifecycle. The preliminary materials cost-analysis indicates that a user could entirely replace every component of the modular cushion several times and maintain a more cost-effective cushion over the complete cushion lifecycle.

Example 1

The modular cushions were compared to three commercially available wheelchair cushions using ISO 16480-4 mechanical tests and an assessment of interface microenvironment conditions. It was found that the modular cushions performed as well as or better than the commercially available cushions.

The different testing methodologies for the assessment of efficacy and performance of wheelchair cushions can generally be categorized as: direct measurements of the cushion and its properties, measurements of the interface between the cushion and the user, and measurements relating to the patient physiology.

The standards outlined in the ISO 16480-2 utilize specific loading and boundary conditions to quantify the response of cushions under these conditions to show the mechanical properties of the cushions. ISO protocols include:

Measurement of the cushion's thickness in response to gradual loading and unloading to generate a hysteresis loop The cushion's force dampening response to a dynamic impact The ability of the cushion to recover back to its original dimensions after a high load is applied Determining if the cushion will bottom-out (no change in compression after an increase in load) in its functional range Measurements of the interface between the user and cushion can help provide additional relevant data for cushion assessment. Interface pressure maps consist of a grid of pressure sensors placed over the cushion, which allow for real-time measurement of the axial pressure and/or force between the user and cushion at many locations over the surface, so as to provide insight into the magnitude and location of high pressure points. In addition to axial pressure, interface shear is also a contributor to the formation of pressure ulcers. As such, interface shear stress mapping over the surface of a cushion would also be informative, though difficult to measure accurately. Nevertheless, this technique provides insight into lateral movement of the user over the cushion and other actions which can produce high shear stress while maintaining relatively constant axial pressure.

In addition to axial and shear pressures, heat and moisture can also contribute to the development of a pressure ulcer and tissue breakdown. A modified rigid cushion loading indenter is a buttock-shaped device used to apply load to cushions, as outlined in ISO 16480-2, for measuring the temperature and humidity level of the microenvironment at the cushion-user interface under load. This test mimics body heat and sweat, in addition to mechanical load, to assess the cushion's ability to dissipate heat and moisture.

For this study, three commonly prescribed control cushions were selected for comparison with test cushions. These cushions were the Jay Medical® Jay® 2 and the Roho® High Profile and Low Profile Dry Floatation® cushions.

The Jay® cushion is a gel-based cushion, with a foam substrate. The cushion uses proprietary Jay Flow™ gel to provide effective pressure relief and some postural support of the user. The gel-based Jay® cushion can malfunction if the gel chamber is pressure punctured; the gel can leak out compromising its pressure relief abilities, and require replacement. Care also must be taken to avoid exposure to cold temperatures, such as a car left outside during the winter overnight, as the gel may freeze.

The air-based Roho® cushions are made of a grid of interconnected rubber air cells. The interconnected cells allow air to pass between the cells, distributing the load applied over the entire cushion. The Roho® cushion must be manually inflated, then deflated to fit the user in a manual, qualitative process that can require a second person to ensure accuracy. Thus these cushions require high maintenance to perform optimally. Moreover, the Roho® cushion does not provide as much postural stability as the Jay® cushion, and likewise can be rendered unusable by a puncture of a single cell. All Roho® cushions employ the same design, however the high profile variation is 4 inches tall, compared to the low profile, 2 inches tall configuration.

Applying 250N of load using the rigid contour loading indenter on the fitted cushion resulted in a 26% drop in peak pressure, and a 32% drop in average pressure over the entire cushion, as compared to the Type III cushion under the same load conditions. However, the rigid contour loading indenter, unlike a real person, is totally rigid.

The sitting microenvironment simulator geometry was cast out of polyurethane casting resin, from a plaster mold made of the rigid contour loading indenter. To deliver the proper load, coupling was used to attach the sitting microenvironment simulator to the materials testing system. The casting resin is rigid, and the other components of the sitting microenvironment simulator do not appreciably affect its interface geometry, thus loading profiles are the same.

Figure 5:
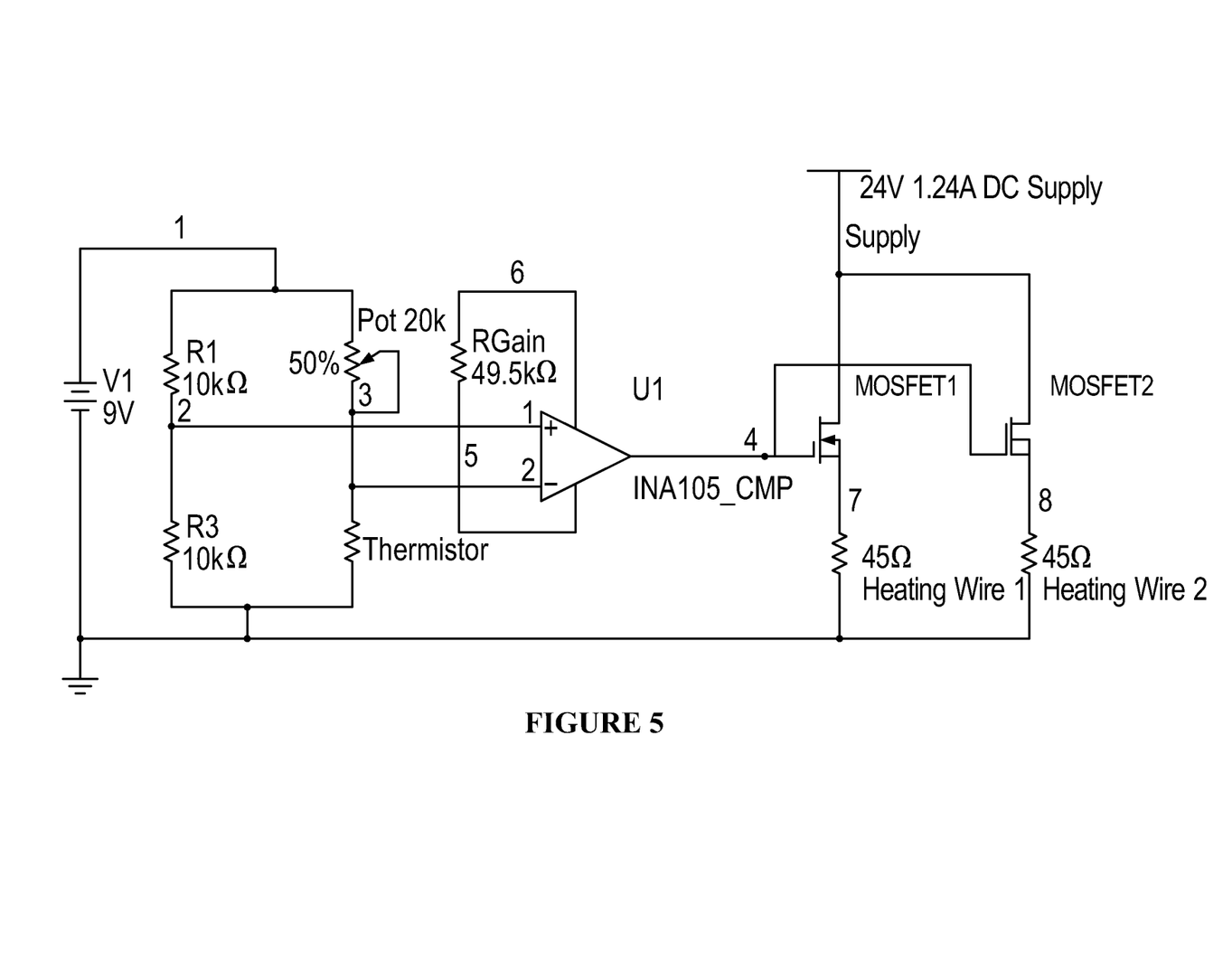
FIG. 5 is an electronics schematic representation of one apparatus useful as the sitting microenvironment simulator.

The sitting microenvironment simulator uses nichrome resistive heating wire sealed to the interface surface using silicone to generate heat. A thermistor embedded in the left ischial tuberosity region forms part of a Wheatstone bridge, along with a potentiometer, which serves as a control circuit to regulate the amount of current that's delivered to the two loops of resistive wire from a 12V, 1.25 A DC power supply, all as shown in FIG. 5. The control circuit has been calibrated using the potentiometer so that when it is exposed to ambient air, the surface temperature of the sitting microenvironment simulator reaches equilibrium at 37.2° C.±1° C.

In order to deliver "sweat" to the interface, no membrane or micro-scale pores are used. Instead, moisture is delivered from an external reservoir using a peristaltic pump that is set to deliver 13 mL/hour of water. This water is pumped through IV tubing down the center of the sitting microenvironment simulator's interface surface. 0.5 mm holes in the IV tube allow moisture to leak from the tube at 13 mL/hour at equilibrium. Once outside the IV tubing, canvas cloth is used to wick the moisture away from the tubing, and over the interface surface in a physiologically relevant manner, in which most of moisture is delivered between the ischial tuberosity regions, and the delivery rate lessens with distance from this maximum.

An assessment was made of the interface microenvironment under relevant conditions of heat, moisture, and load delivery. The indenter and the cushion were set up the materials testing system machine as for rigid contour loading indenter testing. Using a thermometer and hygrometer, ambient temperature and humidity of the air was measured. The IV tubing was filled with water before setting the peristaltic pump to produce a flow rate of 13 mL/hour. The electrical components are then switched on, and the materials testing system set to maintain a load of 300N±10N with the sitting microenvironment simulator turned on. Once 300N of load is achieved (T=0 minutes), measurements of the temperature and humidity at the left ischial tuberosity region of the interface were taken every 5 minutes after the load is applied for 120 minutes. Each of the six cushions underwent 3 separate trials, with at least 60 minutes of recovery time between trials to allow both the cushion to recover, and to allow the canvas cloth which delivers moisture to dry out.

FIGS. 4A through 4D show average temperature and humidity across the 3 trials for each cushion. Plots are shown both with and without their error bars for ease of interpretation. Additional data is provided in Table 2 below.

TABLE 2

Interface Microenvironment Assessment

|  | Fitted Cushion | Type III Cushion | Type I Cushion | Jay ® | Roho ® Low Profile | Roho ® High Profile |
| --- | --- | --- | --- | --- | --- | --- |
| Ambient Conditions | 20.6° C. 17% | 25.5° C. 15% | 25.2° C. 14% | 27.2° C. 14% | 26.6° C. 13% | 24.4° C. 15% |
| $T_{60}$-$T_0$ | 12.8° C. | 7.3° C. | 6.9° C. | 6.1° C. | 4.3° C. | 7.7° C. |
| $T_{120}$-$T_{60}$ | 1.9° C. | −1.1° C. | 0.4° C. | 0.3° C. | −0.6° C. | −2.4° C. |
| $H_{60}$-$H_0$ | −5% | −5% | −3% | −3% | −2% | −4% |
| $H_{120}$-$H_{60}$ | 0% | 5% | 0% | 3% | 4% | 6% |
| Time to 33° C. | 40 min | 35 min | 65 min | 10 min | 15 min | 20 min |
| Time to 12% Humidity* | — | 120 min | — | 115 min | 110 min | 95 min |
| Max. Temp. | 36.2° C. | 33.4° C. | 33.3° C. | 34.6° C. | 33.4° C. | 33.5° C. |
| Max. Humidity* | 11% | 13% | 11% | 12% | 15% | 17% |

Microenvironment testing indicates several differences in cushions' responses. However the standard deviations of both measurements create the potential for overlap between cushions.

The temperature responses indicate that the cushions quickly begin to heat up from ambient temperature before plateauing around 20 minutes into the test. Other than the fitted modular cushion, each cushion gained around 7° C. from the ambient temperature. Once the plateau is reached, the Jay, Type I, and Type III cushions all maintain about the same interface temperature, or increase very slowly. The Type I and Type III baseline modular cushions plateau around 33° C., and the Jay® cushion plateaus around 34° C. The two Roho® air-based cushions did not plateau, but rather peak around 33.5° C. at 20-30 minutes, before losing temperature and cooling to near 31° C. at 120 minutes.

The behaviors between these two groups of responses may be explained by the differences in the cushion's designs. The Roho® cushions have deep open-air grooves between their air cells, potentially allowing air to circulate between the cells, even while it is under load. Air within the cushion can also circulate. These effects combine to give the Roho® cushions very high surface area to lose heat to the surrounding air. By contrast, the Jay® and the modular cushions have relatively low surface areas, and are made of solid materials with lower thermal conductivity than air, not allowing them to lose heat as quickly and reach a higher equilibrium temperature. The small difference in equilibrium temperature between the Type I and III baseline modular cushions and the Jay® cushion may be affected by the higher ambient temperature during the Jay® trials, and by the thermal properties of the cushion itself. The fitted modular cushion did not plateau or peak like the other cushions. It rises quickly to begin, like the others, but the rise in temperature never stops, it only slows. The temperature rises to 36.2° C., and would continue to rise over time, at least until reaching the sitting microenvironment simulator's equilibrium temperature of around 37° C. While the fitted cushion's ball layout is different than that of the Type I or Type III cushion, the properties of the different balls would not be expected to exhibit a dramatic a difference in temperature response. However, a more major factor was likely to be the ambient temperature being nearly 5° C. cooler than the others. Thus, while the Roho® cushions finished at the coolest temperature, and the Jay® finished at the warmest temperature, the three modular cushions stayed cooler for longer, staying below 33° C. for at least 15 minutes longer than the slowest-heating commercial cushion. The Type I and Type III modular cushions reached equilibrium between that of the Jay® and Roho® cushions. Thus, the modular cushions are at least as good as dissipating body heat as the commercially available Jay® cushion.

With respect to humidity, all cushions start out at the ambient air level of humidity, but as they warm, the heat dries out the hygrometer and the interface between the cushion and the sitting microenvironment simulator, reducing the humidity to 10-12%. As water leaks from the IV tube, it is wicked away from it by the canvas cloth. The hygrometer is placed at the left ischial tuberosity, a set distance of a few inches away from the IV tube. The humidity level thus remains low until the damp area of the cloth expands to affect the hygrometer, at which point the humidity begins to rise once again near the end of the test, for all cushions except the Type I and fitted modular cushion. The humidity results represent how quickly the moisture is able to spread across the interface. The Roho® cushions showed an earlier increase in humidity and reached the highest peak. The Type I and fitted modular cushions never saw an increase, which meant that the damp area of the cloth never got close enough to the hygrometer to register a reading.

In practice, this result is has limited physiological relevance, since sweat is constantly produced by skin, just at different rates depending on location. It does not spread outward from a central source. However, the sitting microenvironment simulator does provide some insight into the cushion properties. The Roho® cushions may get wetter faster since later in the test they were also cooler, so the heat wasn't causing as much evaporation, indicating a possible link between the temperature and moisture responses. The surface of the Roho® air cells could have trapped the water more than the Jay® and modular cushions, whose outer surfaces include cloth and foam respectively. Despite increased airflow between the cells of the Roho® cushions, the applied load may have sealed the tops of the air cells to the indenter's surface.

The similarity and relatively high standard deviations of the results of the humidity response limit the extent of the conclusions that can be drawn from them. However, it can be concluded that the three modular cushions appeared to perform at least as well as the commercially available cushions, if not slightly better.

Microenvironmental testing using the sitting microenvironment simulator indicated that, the modular cushions performed on par with the commercially available cushions in terms of interface between the cushion and the user cool and dry. This, in addition to the mechanical properties of the cushion, can reduce the risk of the patient developing a pressure ulcer.

Example 2

ISO Standard 16480 describes standards relating to wheelchair seating. ISO 16480-2 is for "Determination of physical and mechanical characteristics of devices intended to manage tissue integrity-seat cushions" and describes four main tests used to determine the mechanical properties of wheelchair cushions. These tests are designed to assess the hysteresis, impact damping, and recovery properties, as well as the cushion's response to being overloaded.

The ISO 16480-2 mechanical tests utilize two special devices for applying load to the cushion, that are designed to mimic different aspects of human anatomy. The rigid contour loading indenter is designed to match the geometry of the soft tissue of the human seating surface. The rigid contour loading indenter is made of material that is rigid compared to the cushion, and hence will not deform appreciably under test loading, unlike actual human soft tissue. The rigid contour loading indenter is also designed to be easy to manufacture, using conical and spherical geometry to represent the geometry of the thighs and buttock.

The Loaded Contour Jig represents the geometry and loading conditions of the skeleton, specifically the ischial tuberosities and femoral trochanters, on the cushion being tested. The loaded contour jig uses two 2"×2" diameter cylinders placed 6" apart to represent the ischial tuberosities, and two ⅜"×1" diameter disks placed 18" apart (with the ischial tuberosity cylinders centered between them) to represent the femoral trochanters. A 2" thick nylon webbing strap is pulled across these features to mimic semi-compliant soft tissue over the bones.

A loading rig to apply a controlled load to the modular cushion via one of the two indenters is also required. The loading machine must be capable of applying 830N of load vertically though the cushion, with a displacement measurement accuracy of at least 1 mm. A Materials Testing Systems 810® uniaxial servo-hydraulic loading rig, using a 5,000 lb load cell, set to +/−250 lb load range, and +/−63.5 mm displacement measurement range was used in the current project. A wooden box was constructed to house the cushion being tested on a level platform, and to constrain it on three sides, with the front of the cushion open. The cushion indenter was held fixed in space, mounted directly to the load cell, while the cushion, in the wooden box, was mounted to a hydraulic piston that moved it into the indenter from below.

Before each trial, the cushions were pre-conditioned by loading them using the rigid contour loading indenter for 3 cycles of 830N±10N for 120-180 s, and then allowed to recover for 120-180 s. After pre-conditioning, the cushion was allowed to recover for another 300 s. A baseline load of 8-10N was applied for 120 s±10 s, and the displacement measurement zeroed. Load was then increased by 25N/s in steps of 250N±5N to a maximum load of 750N±5N. The load was paused at 250N, 500N and 750N for 120 s±10 s. The cushion was then unloaded by 25N/s in steps of 250N±5N, pausing at 500N, 250N, and finishing at 10N for 120 s±10 s. At each time point, cushion platform displacement was measured. The cushion was then allowed to recover for 300 s before beginning the next of the three trials. Outcome measures were the displacements at the end of each pause in the loading cycle, and the hysteresis coefficients for 250N and 500N of load, as calculated by the following formulae.

$$H_{250} = 1 - \frac{Disp250_{Unloading}}{Disp250_{Loading}} \quad (1)$$

$$H_{500} = 1 - \frac{Disp500_{Unloading}}{Disp500_{Loading}}$$

Two wooden blocks were placed under the back of the platform the cushion rests against, in order to tip the cushion forward by 10°±1°. The angled cushion was then loaded to 500N±10N using the rigid contour loading indenter. The cushion was loaded using load-control mode, so that the materials testing system attempted to keep a constant 500N on the load cell. The displacement measurement was zeroed at 500N. The two wooden blocks were then quickly removed from under the wooden platform, causing it, and the cushion, to fall a short distance, leaving contact with the rigid contour loading indenter. As the cushion fell away from the rigid contour loading indenter, the load cell saw a drop in load. It responds by pushing the now-level cushion back into the fixed rigid contour loading indenter to restore the 500N load. During this response, displacement data from the materials testing system was recorded. The cushion was allowed to recover, with no applied load, for 300 s between trials. Outcome measures for this test were the maximum and minimum accelerations experienced during rapid off-loading.

This test was modified due to the limited response time of the materials testing system. In the ISO test, the cushion, other than the 10° drop, is held stationary, and the rigid contour loading indenter which weighs 500N, and has an attached accelerometer, falls under its own weight as the cushion platform drops from 10° of inclination to level. The materials testing system machine was unable to mimic the speed of this reaction as it attempted to restore the 500N load using its hydraulic piston. Outcome measures for this test were supposed to include properties of the dampening affect such as the damping coefficient, and the number of rebounds above 10% of the maximum acceleration.

Cushions were loaded using the loaded contour jig at 8-10N in order to establish baseline contact and zero the displacement measurement. The load was then increased to 500N±10N for 1,200 s±60 s. Applied load was then reduced back to 8-10N using load-control, to allow the cushion platform to move as the cushion recovers, and maintain contact with the loaded contour jig. The displacement of the cushion was measured just before removal of the 500N load, as well as 25 s±0.5 s and 1,200 s±0.5 s after removal of the 500N load. Additional outcome measures for this test ratio of the displacement at 25 s and 1,200 s after removing the 500N load to the displacement just before the 500N load was removed.

The ISO 16480-2 Recovery Test was modified by using the loaded contour jig throughout the test due to limitations of the materials testing system machine.

Each Overload-Deflection trial was conducted immediately following the end of the Recovery trial for that cushion. With the 8-10N load from the loaded contour jig still being applied, the displacement measurement was zeroed. A 135N±5N load was then applied to the cushion using the loaded contour jig for 300 s±10 s. After this pause, the load was increased to 180N±5N for 300 s±10 s, before reducing the load back to 8-10N. This displacement was measured after each 300 s pause. After each Overload-Deflection trial, all load was removed from the cushion and it was allowed to recover for 300 s before beginning the next Recovery trial. Outcome measures for the Overload-Deflection test are the difference in displacement from 10N of load to 135N of load, and from 135N to 180N.

Load-displacement data was outputted directly from the materials testing system machine for each of the four mechanical tests to determine the ISO 16480-2 outcome measures. The results are summarized in the tables below. Interface pressure data was also taken during all trials and used to fit the modular cushion to the rigid contour loading indenter.

TABLE 3

| Hysteresis Displacement (mm) and Hysteresis Coefficients | | | | | | |
|---|---|---|---|---|---|---|
| | Fitted Cushion | Type III Cushion | Type I Cushion | Jay ® | Roho ® Low Profile | Roho ® High Profile |
| 10N Increasing | 0.67 ± 0.39 | −0.10 ± 0.36 | 0.13 ± 0.15 | −0.01 ± 0.04 | 0.01 ± 0.01 | 1.76 ± 0.97 |
| 250N Increasing | 24.47 ± 0.81 | 31.71 ± 0.33 | 34.28 ± 0.57 | 11.06 ± 1.25 | 27.31 ± 0.59 | 43.38 ± 0.28 |
| 500N Increasing | 34.49 ± 0.81 | 42.08 ± 0.33 | 44.62 ± 0.70 | 14.45 ± 1.26 | 32.31 ± 0.67 | 51.50 ± 0.85 |
| 750N | 40.50 ± 0.88 | 47.29 ± 0.15 | 49.57 ± 0.79 | 17.36 ± 1.21 | 35.14 ± 0.70 | 56.12 ± 0.80 |
| 500N Decreasing | 36.72 ± 0.79 | 43.66 ± 0.17 | 46.22 ± 0.77 | 15.95 ± 1.20 | 33.27 ± 0.69 | 53.80 ± 0.78 |
| 250N Decreasing | 28.19 ± 0.90 | 35.76 ± 0.25 | 38.75 ± 0.61 | 13.15 ± 1.19 | 29.68 ± 0.67 | 49.30 ± 0.74 |
| 10N Decreasing | 1.06 ± 0.96 | 4.09 ± 0.53 | 5.66 ± 0.23 | 3.71 ± 0.61 | 11.34 ± 0.98 | 23.25 ± 0.61 |
| $H_{250}$ | −0.15 | −0.13 | −0.13 | −0.19 | −0.09 | −0.14 |
| $H_{500}$ | −0.06 | −0.04 | −0.04 | −0.10 | −0.03 | −0.04 |

After numerically differentiating the displacement over time data from the materials testing system, the dynamic acceleration plots for all six cushions were similar to FIG. 20. The initial positive spike shows the platform starting to move upward after the blocks are removed from under the cushion, and the piston moves upward to re-establish contact. The negative spike shows the cushion re-establishing contact with the indenter.

TABLE 4

Dynamic Impact Maximum and Minimum Accelerations (mm/s$^2$)

|  | Fitted Cushion | Type III Cushion | Type I Cushion | Jay ® | Roho ® Low Profile | Roho ® High Profile |
|---|---|---|---|---|---|---|
| Max Acc. | 0.027* ± 0.008 | 0.254 ± 0.022 | 0.268 ± 0.005 | 0.273 ± 0.005 | 0.272 ± 0.005 | 0.264 ± 0.007 |
| Min Acc. | −0.005* ± 0.002 | −0.049 ± 0.001 | −0.049 ± 0.002 | −0.087 ± 0.005 | −0.068 ± 0.002 | −0.050 ± 0.002 |

TABLE 5

Recovery Test Displacements T Seconds After Load Removal (mm)

|  | Fitted Cushion | Type III Cushion | Type I Cushion | Jay ® | Roho ® Low Profile | Roho ® High Profile |
|---|---|---|---|---|---|---|
| T = 0 s | 63.15 ± 0.60 | 63.50 ± 0.00 | 63.50 ± 0.00 | 37.34 ± 3.91 | 41.51 ± 5.93 | 63.50 ± 0.00 |
| T = 25 s | 8.37 ± 2.30 | 17.31 ± 0.25 | 23.16 ± 3.23 | 20.57 ± 2.62 | 26.43 ± 0.90 | 63.50 ± 0.00 |
| T = 1,200 s | 4.55 ± 0.71 | 0.91 ± 1.28 | 4.44 ± 1.58 | 11.98 ± 3.81 | 9.61 ± 4.42 | 19.59 ± 2.75 |
| $\frac{T = 25 \text{ s}}{T = 0 \text{ s}}$ | 0.13 | 0.27 | 0.36 | 0.55 | 0.64 | 1.00 |
| $\frac{T = 1,200 \text{ s}}{T = 0 \text{ s}}$ | 0.07 | 0.01 | 0.07 | 0.32 | 0.23 | 0.31 |

TABLE 6

Deflection-Overload Displacements for Specified Loads (mm)

|  | Fitted Cushion | Type III Cushion | Type I Cushion | Jay ® | Roho ® Low Profile | Roho ® High Profile |
|---|---|---|---|---|---|---|
| 10N | 0.44 ± 0.22 | 0.19 ± 0.19 | 0.55 ± 0.42 | 0.50 ± 0.38 | 0.25 ± 0.41 | 0.77 ± 0.37 |
| 135N | 28.55 ± 0.23 | 35.73 ± 0.28 | 39.48 ± 0.26 | 27.97 ± 0.89 | 35.65 ± 1.40 | 63.50 ± 0.00 |
| 180N | 35.39 ± 0.25 | 42.88 ± 0.37 | 47.02 ± 0.39 | 29.67 ± 0.86 | 36.16 ± 1.42 | 63.50 ± 0.00 |
| 135N-10N | 28.12 | 35.54 | 38.92 | 27.47 | 35.39 | 62.73 |
| 180N-135N | 6.84 | 7.15 | 7.54 | 1.70 | 0.51 | 0.00 |

Each of the four ISO test protocols are designed to test a specific mechanical property or ability of wheelchair cushions that is clinically relevant for the end user's experience, and the cushion's functionality. In order to compare the modular cushions to the three commercially available cushions, their responses were evaluated in each of the four ISO tests.

The Hysteresis Test is designed to examine how the cushions behave while ramping up or ramping down the load applied. An ideal cushion has no hysteresis—it's not dependent on past loads when measuring how it compresses under a given load. The cushion should be able to respond to and adapt to its current situation quickly, without excessive hysteresis. This is highly dependent on the viscoelastic and fluid mechanic properties of the cushion's materials. As defined by Equation 1, a hysteresis coefficient of 0 corresponds to the case where the loading and unloading displacements are the same. As the unloading displacement increases relative to the loading displacement, the hysteresis coefficient becomes more negative. Therefore, the closer to 0 the hysteresis coefficients for each cushion are, the less hysteresis it experiences, and the better it performs. The two cushions that are the most solid, the fitted modular cushion and the Jay® cushion have more negative hysteresis coefficients when compared to the cushions that are mostly fluid, the Roho® cushions and the Type I and Type III modular cushions. For both hysteresis coefficients, the three modular cushions fall between the Jay® and Roho® cushions in hysteresis performance, putting them on par with the commercially available cushions.

The Dynamic Impact tests are designed to examine how well the cushions will absorb an impact, specifically simulating a wheelchair falling a short distance, such as if a user were to roll off a curb. The test should generate a damped oscillation pattern which can be categorized. However, due to the limitations of the materials testing system, it cannot simulate this scenario. In the current study the tests were limited to the "impact" of the cushion re-establishing contact with the rigid contour loading indenter, a single deceleration. The spikes of maximum acceleration for the cushions were all within 0.02 mm/s$^2$ of each other. This positive spike is caused as the piston starts to move, and at this point in the test, the cushion is not in contact with the rigid contour loading indenter, and has no effect on the motion of the piston. The spike in minimum acceleration shows how quickly the piston slows down as contact is re-established. The smaller (less negative) the acceleration during the minimum spike, the better the cushion is at absorbing the "impact," and the less peak force is transmitted to the rigid contour loading indenter. Both the Type I and III modular cushions perform better than or as well as all three commercial cushions. The Dynamic Impact tests for the fitted modular cushion were performed using a different load cell (set to the same range) as the other five cushions, for equipment availability reasons. As such, this load cell sent a different control signal to the materials testing system, which is very likely the cause of the Fitted Cushion accelerations being an order of magnitude lower than the other five cushions. Based on the results of the other tests, it could be predicted that the Fitted Cushion, being slightly more solid than the baseline cushions, would perform slightly worse than the baseline modular cushion, but still better than the Jay® or Roho® cushions.

The Recovery test is designed to determine how quickly the cushion will spring back to its resting state after a load that's been applied for a long time has been removed. A perfect cushion has little to no time-dependence in its response to load, and would recover to its full thickness as quickly as possible, so that it would be able to fully absorb the next application of load. The Recovery test examines the displacement ratios just before the 500N load is removed to 25 s and 1,200 s after load removal. An ideal cushion would fully recover, while an exceptionally poorly performing cushion would not have recovered at all. The three modular cushions all performed better than the three commercial cushions, with the fitted cushion performing the best of all. The Roho® air cushions performed most poorly. Their relatively low level of inflation (performed to manufacturer specifications) did not result in much restoring pressure to re-fill the compressed air chambers. The Roho® High Profile cushion did not recover at all after 25 s, and had recovered just over two thirds of its lost thickness after 1,200 s. The Type I baseline modular, Type III baseline modular, and High Profile Roho® cushions all reached 63.5 mm displacement during the 500N loading period using the loaded contour jig. Displacements for these cushions may have been higher, but the piston's displacement measurements became saturated after 63.5 mm. This would only have affected the T=0 s displacement, and could only have potentially made the recovery ratios for these three cushions worse, meaning the Fitted modular cushion performed the best of all six cushions.

The Deflection-Overload test checks the cushion's ability to continue deforming under high loads, i.e. to prevent "bottoming out," where despite increased loading, the cushion doesn't deform any more to absorb that energy. A cushion which performs well at this test should have a high change in displacement between 135N and 180N of load, showing that it continued to deform and absorb that energy. The three modular cushions performed better than the three commercially available cushions, continuing to deform by more than 6 mm. The Jay, the best of the commercial cushions, deformed by less than 2 mm between 135N and 180N. The air cushions performed poorly, deforming so much under 135N that very little, or no, deformation was seen as the load was increased to 180N. The loaded contour jig puts most of the load on the two ischial tuberosity cylinders, which are able to compress all the air out of a small number of the Roho® air cells. The Roho® cushions depend on the entire cushion to support the load, as the air moves freely between the cells. The Jay® cushion, has its gel-filled chamber supported by very rigid foam, which does not deform appreciably under load. The three modular cushions performed well since they are constrained fluid based, allowing only a few balls under the LOADED CONTOUR JIG to support the entire load, while the surrounding soft foam continues to deform to absorb the load. Thus the modular cushions performed best under deflection-overload testing.

The modular cushions performed better than the commercially available cushions in Dynamic Impact, Recovery, and Deflection-Overload testing. In the Hysteresis test they performed comparably to the commercial cushions. The ISO mechanical tests showed that the modular cushions, and specifically the fitted modular cushion, perform mechanically at least as well as the commercially available cushions, and in most cases perform better. This, combined with their lower projected cost, shows the modular cushions are viable as both more effective and less expensive than the cushions that are currently on the market.

Any tests of the effectiveness under loading conditions of the balls and/or cushions described herein were in accordance with protocols from the International Organization for Standardization (ISO), Report 16480-2. Standard tests include assessment of cushion hysteresis, dynamic impact, recovery, and overload properties. A cushion's response to a warm and humid microenvironment, another important factor in pressure ulcer development, was assessed using a test rig and protocol modified from a device and protocol proposed by Ferguson-Pell et al. Comparative test of the inventive cushions, comprised of balls with varying internal compositions, were based against commercially-available cushions similar to those described in the background section above.

Although the present embodiments have been illustrated in the accompanying drawings and described in the foregoing detailed description, it is to be understood that the invention is not to be limited to just the embodiments disclosed, and numerous rearrangements, modifications and substitutions are also contemplated. The exemplary embodiment has been described with reference to the preferred embodiments, but further modifications and alterations encompass the preceding detailed description. These modifications and alterations also fall within the scope of the appended claims or the equivalents thereof.

Having thus described the invention, we claim:

1. A method of manufacturing a customized cushion that reduces risk of formation of pressure ulcers in a user, the method comprising:
   a) creating a pressure map based upon the user;
   b) associating portions of the pressure map with a modular array of regularly spaced gel balls arranged within a uniform array;
   c) determining individual loading of each ball based upon location of each ball relative to the pressure map and concurrently determining the average pressure on a group of adjacent balls based upon the location of the group of adjacent balls relative to the pressure map; and
   d) adjusting viscosity of each ball within the array based upon the determinations in step (c) and providing it to a foam substrate.

2. The method of claim 1 further comprising enclosing the balls within a cushion pad.

3. The method of claim 1, wherein step (c) includes assigning at least one of the individual loading of each ball and the average pressure on a group of adjacent balls to a series of incrementally increasing target force ranges.

4. The method of claim 1 further comprising replacing individual balls within the foam substrate upon failure.

* * * * *